US008685715B2

(12) United States Patent
Minter et al.

(10) Patent No.: US 8,685,715 B2
(45) Date of Patent: Apr. 1, 2014

(54) AGGLUTINATION REACTION SYSTEM (75) Inventors: Stephen John Minter, Stockport (GB);
Damian Joseph Peter Bond, Bacup (GB); Carolyn Jennifer Ruddell, Heswall (GB)

(73) Assignee: Platform Diagnostics Limited, Ossett (GB)

( * ) Notice: Subject to any disclaimer, the term of this patent is extended or adjusted under 35 U.S.C. 154(b) by 1311 days.

(21) Appl. No.: 11/718,324

(22) PCT Filed: Oct. 28, 2005

(86) PCT No.: PCT/GB2005/004166
§ 371 (c)(1),
(2), (4) Date: Apr. 30, 2007

(87) PCT Pub. No.: WO2006/046054
PCT Pub. Date: May 4, 2006

(65) Prior Publication Data
US 2009/0035743 A1    Feb. 5, 2009

(30) Foreign Application Priority Data
Oct. 28, 2004  (GB) .................................. 0423885.3

(51) Int. Cl.
C12M 1/34    (2006.01)

(52) U.S. Cl.
USPC ..................................... 435/288.5; 435/287.1

(58) Field of Classification Search
USPC ........................................... 435/287.1, 288.5
See application file for complete search history.

(56) References Cited

U.S. PATENT DOCUMENTS

| | | |
|---|---|---|
| 3,951,606 A | 4/1976 | Moyer et al. |
| 4,586,335 A | 5/1986 | Hosoda et al. |
| 4,756,884 A | 7/1988 | Hillman et al. |
| 4,963,498 A | 10/1990 | Hillman et al. |
| 5,231,035 A | 7/1993 | Akers, Jr. |
| 5,736,188 A | 4/1998 | Alcock et al. |
| 5,756,362 A | 5/1998 | Durst et al. |
| 5,786,220 A | 7/1998 | Pronovost et al. |
| 5,837,546 A | 11/1998 | Allen et al. |
| 6,235,241 B1 | 5/2001 | Catt et al. |
| 6,673,533 B1 | 1/2004 | Wohlstadter et al. |
| 2002/0187071 A1 | 12/2002 | Law |

FOREIGN PATENT DOCUMENTS

| | | |
|---|---|---|
| EP | 0 057 110 A2 | 8/1982 |
| EP | 0321736 A2 | 6/1989 |
| EP | 0 485 368 A2 | 5/1992 |
| EP | 0212314 B1 | 4/1994 |
| EP | 0456699 B1 | 4/1995 |
| EP | 0 999 786 | 2/1999 |
| EP | 0 596 104 B1 | 7/2002 |
| GB | 2310493 A | 8/1997 |
| WO | 9009596 A1 | 8/1990 |
| WO | 93/22054 A1 | 11/1993 |
| WO | 93/24231 A1 | 12/1993 |
| WO | 9506240 A1 | 3/1995 |
| WO | 95/13531 A1 | 5/1995 |
| WO | 96/05510 A2 | 2/1996 |
| WO | 98/43739 A2 | 10/1998 |
| WO | 9935497 A2 | 7/1999 |
| WO | 0033063 A1 | 6/2000 |
| WO | 2004083859 A1 | 9/2004 |
| WO | WO 2004083859 A1 * | 9/2004 |

OTHER PUBLICATIONS

Gibbons et al. "Patient-side immunoassay system with a single-use cartridge for measuring analytes in blood", Clin. Chem. 1989, 35(9):1869-1873.*

* cited by examiner

Primary Examiner — Bin Shen
(74) Attorney, Agent, or Firm — Janet Sleath; Speckman Law Group PLLC (57) ABSTRACT The present invention provides an agglutination based assay system for determining the presence and/or amount of analyte in a sample comprising a test device having one or more capillary pathways comprising detection regions adapted for non-visual detection of a sample which is releasably engageable with a reader which comprises detection means for detecting the sample at the detection regions in each of said capillary pathways and electronic means for indicating the presence and/or amount of analyte.

28 Claims, 3 Drawing Sheets

AGGLUTINATION REACTION SYSTEM

REFERENCE TO RELATED APPLICATIONS

This application is a continuation of International Patent Application No. PCT/GB2005/004166, filed Oct. 28, 2005, which claims priority to UK Patent Application No. 0423885.3, filed Oct. 28, 2004.

INTRODUCTION

The present invention relates to an agglutination based assay system for detection of analyte in a sample. Also provided are a test device and reader of the assay system, and an assay method using the system, and kits comprising components of the invention.

BACKGROUND TO THE INVENTION

Immunoassays, and in particular techniques such as the radioimmunoassay and enzyme immunoassay, have revolutionised diagnostic medicine. Such assays are based upon the detection of antibody-antigen interactions. Numerous detection systems are available, including the use of enzyme labelled antigens, antibodies or complexes thereof, which require incubation with specific substrates in order to measure the end-point either colour metrically or flourescently.

Whilst these assays are sensitive, the detection systems are complex, and therefore expensive. Typically, the detection systems require several washing steps, meaning that the assays are generally unsuitable for point-of-care type assessment.

Agglutination immunoassays are well known in the art, and rely upon agglutination of particles to which an antigen or antibody is bound to indicate the presence of the corresponding antigen or antibody in a sample. In one of the simpler forms of an agglutination assay, antibodies to a particular analyte are bound to a bead or other visible material. For example, in the latex agglutination reaction, the presence of analyte present in the system is detected, bound to the surface of the latex beads. Typically, the antibody will be divalent, thus causing the latex beads to form clumps in the presence of an analyte. Such clumps indicate a positive result, and can be seen with the naked eye.

Bio-Diagnostics Ltd, in their patent application No. WO 99/35497, disclose a agglutination based assay device for identifying blood groups. The device incorporates four blood group testing channels, namely three capillary channels which part way along their lengths are formed into one or other of the indicators A, B, or O and a further capillary channel which incorporates an indicator in the form of a + symbol, indicative of rhesus status. Upstream of each indicator, the channels have an agglutination system which causes blood corresponding to the indicator of the channel to agglutinate and impede flow in the channel. Thus, when a sample is introduced, blood will flow unhindered along the capillary channels, and will cause the indicators to be coloured red. Where the blood is of Group A, for example, an agglutination will take place, preventing blood from flowing into the indicator portion of the channel. Thus, the indicator will not become coloured red, but will remain white. In this way, the blood group can be determined visually. However, there is room for human error in such a test, due to reliance on the user to correctly read and interpret the visual result. The assay is also reliant upon the agglutination causing a total blocking of the capillary, therefore erroneous results may arise if the agglutination reaction is weak or if the sample volume is insufficient to fill all the capillaries. Also, the result may be unstable, yielding a different result if read at a later time.

WO04/83859 describes a capillary based agglutination assay, comprising a capillary pathway which contains a reagent system capable of causing agglutination with the analyte. The reagent system comprises an antibody bound to either the capillary walls at a predetermined location, or antibody bound to beads which are placed in the capillary system at a predetermined location. Upon application to the capillary pathway, a sample (and optionally ancillary reagents) flows along the pathway until it reaches the agglutination reagent system. If analyte is present, agglutination will occur, preventing or slowing further flow of the sample along the capillary. Detection means for the presence of the sample at the downstream end of the pathway are effected after a predetermined time from application of the sample—if no sample can be detected, then analyte is present, indicating a positive result. This device uses latex beads as the agglutination means.

The present invention aims to provide an improved agglutination based assay system.

SUMMARY OF THE INVENTION

Thus, in a first aspect of the present invention there is provided a test device for use in an agglutination based assay for determining the presence and/or amount of analyte in a sample, comprising one or more capillary pathways which receive the sample and/or reagent and which extend from an upstream end toward a downstream end and which comprise one or more detection regions, wherein the test device is releasably mountable in a reader which comprises detection means for non-visual detection of liquid at one or more of the detection regions in each of said capillary pathways to provide a pattern of liquid flow to the detection regions, and electronic means for indicating the presence and/or amount of analyte based upon the pattern.

In a second aspect of the invention, there is provided a reader for use in an agglutination based assay for determining the presence and/or amount of analyte in a sample, and in which a test device may be releasably mounted, the reader comprising detection means for non-visual detection of liquid at one or more detection regions in each capillary pathway of the test device to provide a pattern of liquid flow to the detection regions, and electronic means for indicating the presence and/or amount of analyte based upon the pattern.

In a third aspect of the present invention, there is provided an agglutination based assay system for determining the presence and/or amount of analyte in a sample, comprising a test device comprising one or more capillary pathways which receive the sample and/or reagent and which extend from an upstream end toward a downstream end and which comprise one or more detection regions and being releasably mountable in a reader, the reader comprising detection means for non-visual detection of liquid at one or more of the detection regions in each of said capillary pathways of the test device, to provide a pattern of liquid flow to the detection regions, and electronic means for indicating the presence and/or amount of analyte based upon the pattern.

The present invention thus provides a system in which the test device and reader are separate, with the test device being releasably mountable in the reader for performance of an assay. This has the advantage that the test device may be a disposable single-use type device, but the reader element of the system, which is typically more complex and expensive to manufacture, does not have to be discarded at the same time. This not only enables the cost of providing the system to be lowered, but also enables improvements or alterations to be made to each component of the system without requiring replacement of the whole system. In addition, more sophisticated readers may be employed, and test devices may be provided in bulk with a single reader.

By employing a reader, the system of the invention enables the results of the system to be obtained in a non-visual manner, thus reducing the possibility of human error in reading the results directly from a test device.

Agglutination based assays of the present invention include assays for detecting the presence, absence or amount of an analyte based upon agglutination caused upon contact of a sample with agglutination reagents. In the present invention, the agglutination based assay is carried out in a capillary pathway which receives the sample and reagent. The reagents include both the agglutination reagents and any other agents (such as buffers) necessary for the assay. The latter include, for example, an electrolyte (either solid, causing the liquid to become conductive upon dissolution, or pre-dissolved, in the form of a buffer) or fluids which aid flow of reagents/sample along the capillary pathway, or increase the volume of the sample. Suitable fluids include buffers such as PBS pH 7.4, and physiological saline.

Reagents may be pre-applied to the test device at pre-determined positions, for example during manufacture, or may be provided separately to the test device, for example in a container or vial, and introduced into the test device before or during an assay, either with, before or after introduction of a sample.

Where reagents are pre-applied, this will typically be to any part of the test device which comes into contact with the sample, which will therefore typically be all or part of a zone at which sample is introduced or a capillary pathway. Preferably, any pre-applied reagent is present upstream of a detection region. For those reagents which are introduced after the start of an assay, it may be preferable to provide them separately and introduce them directly to a zone or capillary pathway. This may be the case with, for example, chase fluids.

The test device of the invention may comprise at least one capillary pathway, but preferably two, one being the assay pathway and the other being a control pathway. However, it is envisaged that additional pathways may be provided, where it is desired to test multiple samples in a single unit, or a single sample for multiple analytes, for example in blood group analysis. The test device of the invention is typically of a size which enables it to be hand-held. It will preferably be a single-use type device, so that it is used for the performance of one assay and then discarded.

Each capillary pathway has an upstream and a downstream end, and preferably has a zone, or well, at the upstream end to receive the sample/reagents. The zone may comprise a pad to which the sample/agglutination reagents are applied, and from which they enter the capillary pathway. The pad may be formed of absorbent material, preferably fibrous material, e.g. cellulose. Fibrous pads may exert a counter capillary force to the capillary pathway and the selection of pad material will depend on the dimensions and surface treatment of the capillary pathway since these determine the capillary force. Alternatively, a one-way valve may be provided in the zone at the entrance to the capillary pathway, so that the sample/reagents applied to the zone can enter, but not exit, the pathway upon opening of the valve. Alternatively, a pipette or other suitable device may be used to apply the sample/reagent directly into a pathway.

In each capillary pathway are one or more detection regions, at which the presence or absence of liquid by detection means in the reader is monitored. The detection regions are pre-determined positions, preferably down stream of any pre-applied reagent. By measuring the rate of flow along a known distance within the capillary pathway, for example as defined by detection regions, a quantitative result regarding the analyte in a sample is obtained by measuring the rate of flow along the capillary. Thus, the greater the amount of analyte in a sample, the stronger the agglutination reaction will be, and the slower the rate of flow along the pathway. An estimate of the amount of analyte can be made by comparing the rate of flow to a calibration chart or algorithm.

As the detection regions are the positions in the capillary pathways at which the detections means monitor the presence or absence of sample, they may be appropriately adapted, or comprise any means necessary, for the detection means to function. This will of course depend on the nature of the detection means used, but for example where the detection means consists of an electronic circuit, the detection regions may comprise electrodes or such which come into contact with any sample in the detection region, thus completing a circuit. Alternatively, where the detection means use light transmission, the regions may be transparent.

The length of each capillary pathway will be dictated by the time scale of the agglutination reaction, in combination with factors such as the internal cross sectional area of the pathway and the nature and flow rate of the sample and reagents. It must have at least sufficient length to allow time for an agglutination reaction to take place, if analyte is present. Typically, the length of the pathway will be in the region of 10-500 mm, more preferably 35-45 cm. The capillary pathways may have any cross-section, such as circular, square or triangular, based upon manufacturing and flow criteria. The pathways may, in section, be in the form of an equilateral triangle with a side length of 50 to 1000 μm.

Preferably, where two or more pathways are provided in a single test device, they extend in parallel to each other, preferably linearly. For comparison purposes, it is preferred that each such pathway is the same length from at least an upstream end to a detection region, preferably the downstream most detection region. It is particularly preferred that the pathways run in parallel with each other (preferably linearly) over their entire lengths. For convenience, each pathway may not necessarily be linear, but may take any form to suit the size and shape of the test device. Thus, each pathway may take a series of bends or curves along its length. Whilst any form which allows flow of the reagents/sample is acceptable, a preferred form comprises a series of parallel linear pathways connected by a 180 degree bends. Alternatively, each pathway may be provided as a separate formation on the unit.

The test device may be made of any suitable material, such as polycarbonate, polystyrene, or injection moulded plastic, optionally transparent. The capillary pathways are preferably formed as open-topped channels in the surface of the unit, and closed by a fixing of membrane (e.g. of polyester), or seal, thereto, which is preferably hydrophilic in nature. This may be affixed to the body of the unit by any suitable means, such as a hydrophilic adhesive, most preferably one that does not "outgas" or "creep". Any means used preferably do not contain components (e.g. cyanides) that denature proteins otherwise the function of the test device may be impaired. The plastics material from which the unit is moulded may be hydrophobic, with the capillary pathways being optionally treated during manufacture with a hydrophilic reagent, e.g. by washing in a 0.1-10% of Tween 20. The agglutination and other reagents may then be provided in the open-topped pathways.

The test device is releasably mountable in a reader such that upon performance of an assay, the reader and test device become a temporarily integrated device. Thus, the reader and/or test device comprise means, or are arranged such that, upon mounting the detection means of the reader can communicate with the detection regions, preferably through contact. Although not strictly necessary, the means on one or both of the test device and reader may allow for engagement of the components, for example by a securing or locking mechanism. In a simple embodiment, the means comprise in the test device a formation (e.g. a step formation) for locating the unit on a cooperating step in the reader.

The reader comprises detection means for determining the presence or absence of sample at pre-determined positions in the capillary pathways, herein defined as detection regions. The detection means used in the present invention are non-visual, meaning that presence or absence of sample at the detection regions is determined by means other than the naked eye. This reduces the effect of human error, and also, in a point-of-care environment, means that continued monitoring during the performance of an assay by the user is not necessary. Further, the result is permanent and stable.

The detection means will detect the presence or absence of any liquid present in a detection region. The liquid will typically be a reagent and/or sample as described herein, but may include other test liquids used for control purposes or to determine the operability of the unit.

The detection means communicate with one or more of the detection regions in a capillary pathway, to determine the presence or absence of liquid. The results obtained, in the form of a yes/no indication for each detection region, form a pattern which is interpreted by the electronic means into presence and/or amount of analyte.

Any convenient form of detector means may be employed in accordance with the invention. These include optical means such as reflectometers, electrical means, and means for the application of methods such as measurement of light scattering, fluid detection, turbidometry, and nephelometry. Preferred detections means include the electronic optical detection means which may, for example, comprise an array of Light Dependent Diodes (LDDs) or Light Sensitive Resistors. It will be appreciated that, depending on the analyte being determined by the assay, certain of the light sensitive elements will receive light (i.e. those at the detection regions of capillaries along which sample flow has not been arrested). Software is associated with the electronic optical detector which allows the analyte to be determined from the particular signals provided by the electronic optical detector.

Conveniently, the preferred electronic optical detector is of the type used for reading barcodes by light transmission (as opposed to light reflection). In such an embodiment, the detection regions of the test device may be optically transparent so that the presence or otherwise of sample at a detection region may be determined by providing a source of illumination on one side of the test device and electronic optical detector on the other side of the unit. Conveniently the test device may be produced from a light transparent material (e.g. polycarbonate).

The detection means may be programmed to detect the presence of sample reaching a detection region by way of confirmation that the device is functioning properly. Put another way, if sample is not detected in a detection region of a capillary pathway, typically a control capillary, then it must be assumed that the test device is not functioning correctly so that the test will need to be repeated with a fresh test device. It is also preferred to include detection means to detect the presence of sample at an upstream region of the capillary pathways to ensure that the sample has entered these pathways, again by way of a confirmation that the unit is functioning properly.

In order to interpret the pattern of results obtained by the detection means, electronic means are provided. These typically comprise signal processing and display means, optionally together with a power source or means for connection to a power source. The power source may be one which is activated by application, as described in WO04/85389. Alternatively the power source may be a conventional battery.

The electronic means are capable of converting the pattern of results from the detection means to a readable output on a display. Preferably, the electronic means includes a timer which is activated at an appropriate point in the test. Thus, the electronic means communicates with the detection means, converting the result to a digital or other signal. This signal is then transmitted to a display device, which will present the signal is a readable format. This may be a yes/no type result, in the form of words or signs, or may be a quantitative result providing a value which is indicative of the amount of analyte present. Preferably in the latter case, a numerical value is provided such that no further interpretation of the results is necessary.

The agglutination reagents used in the assay may be any which are suitable to use in a capillary pathway, with the type of sample and analytes mentioned herein. Typically, the agglutination system will comprise binding partner having a preferential affinity for the analyte to be detected, bound to an agglutination particle. Binding of the binding partner to analyte will cause agglutination of the agglutination particles. The binding partners may be any substance having a preferential affinity for a predetermined target, (i.e. is specific for that target). Binding partners therefore include monoclonal or polyclonal antibodies, antigens, proteins including enzymes or other binding proteins, aptamers, oligonucleotides, sugars, and fragments thereof. The binding molecules are selected from the above based upon the nature of analyte and agglutination particle, such that they are capable of binding each, as appropriate.

The agglutination particles bound to the binding partners may be biological or non-biological, for example microorganisms, cells, macromolecules, gold particles, beads, (preferably latex), charcoal, kaolinite, or bentonite. Most preferably, the agglutinable particle is a cell, in particular a red blood cell, and is preferably that naturally present in the sample to be analysed. The red blood cells may be derived from any source, although preferred sources are guinea pig and turkey. Prior to use, the red blood cells are coated with antibody, and may be preserved, or fixed, using any suitable method.

Whilst it is preferred that the binding molecules of the reagents bind their targets directly, this is not strictly necessary, and the binding may take place via an intermediate, such as an analyte binding molecule. The intermediate might be naturally present in a sample, or may be separately provided. These include receptors, antibodies, antigens, binding molecules, hormone receptors, oligonucleotides, sugars, aptamers, etc.

The present invention is suited to the detection of any analyte, including proteins, antigen, antibody, oligonucleotide, hormone, aptamer, sugar, or combinations and fragments thereof, organisms such as fungus, bacteria, viruses, protozoa, multicellular parasites, or fragments thereof, or therapeutic and non-therapeutic drugs.

The present invention is suitable for testing bodily fluid samples, such as urine, whole blood, a blood fraction such as plasma, semen, sweat, saliva, amniotic fluid, cerebrospinal fluid, pleural fluid, gingival fluid, cyst extract, and tissue extracts.

In an embodiment of the invention, there is provided a system for determining the blood group characteristic of a blood sample comprising i) test device having a plurality of separate capillary pathways along which blood will flow from upstream to downstream ends thereof, said pathways having detection regions at which the presence or absence of blood may be detected, and said testing pathways further including reagents which will cause agglutination of blood in at least one but not all, of the pathways in a combination dependent upon the blood group characteristic of the blood, ii) detection means for detecting the presence of blood at the detection regions in each of said capillary pathways so as to provide a pattern of blood flow to the detection regions;

iii) electronic means for identifying the blood group characteristic from the pattern determined in step ii).

In this embodiment, the invention employs a test device incorporating reagents that will arrest or retard blood flow along at least one of the capillary pathways but allow blood to continue at least along one further capillary pathway to reach the detection region thereof in an overall combination which is dependent upon the blood group characteristic being determined for the blood sample under test. In an alternative embodiment, the reagents may be introduced with or after the blood sample.

In another embodiment, there is provided a method of determining the blood group of a blood sample, comprising the steps of:

i) providing a system as hereinbefore described ii) introducing into an upstream end of each capillary pathway reagents which will cause agglutination of blood in at least one but not all of the pathways, in a combination dependent upon the blood group characteristic of the blood;

iii) introducing blood into an upstream end of the capillary pathways;

iv) detecting the presence of blood at detection regions of the capillaries so as to determine a pattern of blood flow within the capillary pathways;

v) using electronic means to identify the blood group characteristic from the pattern determined in iii).

Preferably, the test device of the system comprises at least 3, preferably at least 4 and more preferably 5 capillary pathways, such that each blood group may be tested for, together with a control.

Electronic optical detection is the preferred method used to determine the combination of capillaries for which blood flow has and has not received the detection region of the test device. This combination will uniquely identify the blood group characteristic under test and its determination allows a signal to be provided by the electronic means.

In these embodiments, it may be more preferred that the signal is employed as part of, and in accordance with, an overall patient management system with electronic safeguards to prevent blood of incorrect type being administered to a patient. Thus for example, such a patient management system may comprise a computer (or other electronic processing and storage means) which:

(a) stores a previously determined blood group characteristic of the donated blood under test;

(b) electronically receives the blood group characteristic result of the donated blood from the system of the invention;

(c) compares the information for (a) and (b) to confirm or otherwise that the blood to be donated is of the same blood group characteristic as that previously recorded;

(d) stores information about the blood group characteristic of the patient to whom the blood is to be donated; and (e) provides a warning output if the blood is of the wrong type for administration to the patient.

Thus, for example, the system may be such that an identifier number for the patient must be entered into the patient management system before the blood can be administered. The patient identifier number is linked to the patient's blood group characteristics which, if incompatible with those determined for the blood sample under test, causes a warning (e.g. audio and/or visual) to be generated. A further possibility would be for the blood to be administered to have to flow through a computer controlled valve which would not be opened if the patient management system determined that the blood that was going to be administered was not of the correct type for the patient being treated.

By way of further example, the blood test device may be one that is employed for determining whether blood is of Group A, B, AB or O together with the Rhesus characteristic (positive or negative) of the blood. For this purpose, the test device may have four blood testing capillary pathways, namely one each for arresting blood in accordance with the following Table 1. The reagent system employed in each capillary pathway may be an agglutination system, e.g. monoclonal antibody as also indicated in the Table.

TABLE 1

| Capillary Pathway No. | Reagent Arrests Blood with Characteristic | Reagent System |
|---|---|---|
| No 1 | Group A | Anti-A |
| No 2 | Group B | Anti-B |
| No 3 | Group 0 | None |
| No 4 | Rhesus + ve | Anti-D |

If the blood is of Group "A Positive" then blood in tracks 1 and 4 will be arrested, allowing blood in tracks 2-3 to reach the detection regions. Thus the presence of blood at the detection regions of tracks 2, 3 is confirmation that the blood is "A Positive". In the case of blood that is "AB Negative" then blood in tracks 1 and 2 will be arrested, allowing blood in tracks 3-4 to reach the detection regions. Different combinations obviously apply to other blood groups. Electronic optical detection is used to determine the combination of capillaries for which blood flow has and has not reached the detection region of the test device. This combination will uniquely identify the blood group characteristic under test and its determination, by the optical detection arrangement, allows a signal to be provided which may then be employed in a number of ways, as described more fully below.

In a further aspect, kits relating to the invention may be provided, comprising either one or more test devices and optionally sufficient reagent for the same number of assays may be provided, preferably individually packaged, and materials and apparatus as mentioned above including a reader, buffers, reagents, application means (such as pipettes), instructions, charts, desiccants, control samples, dyes, batteries, electronic means and a computer.

BRIEF DESCRIPTION OF THE DRAWINGS

The present invention will now be described by way of a specific, non-limiting example, with reference to FIG. 1 which is an exploded perspective view of one embodiment of test device employed in the present invention.

DETAILED DESCRIPTION OF THE INVENTION

Figure 1:
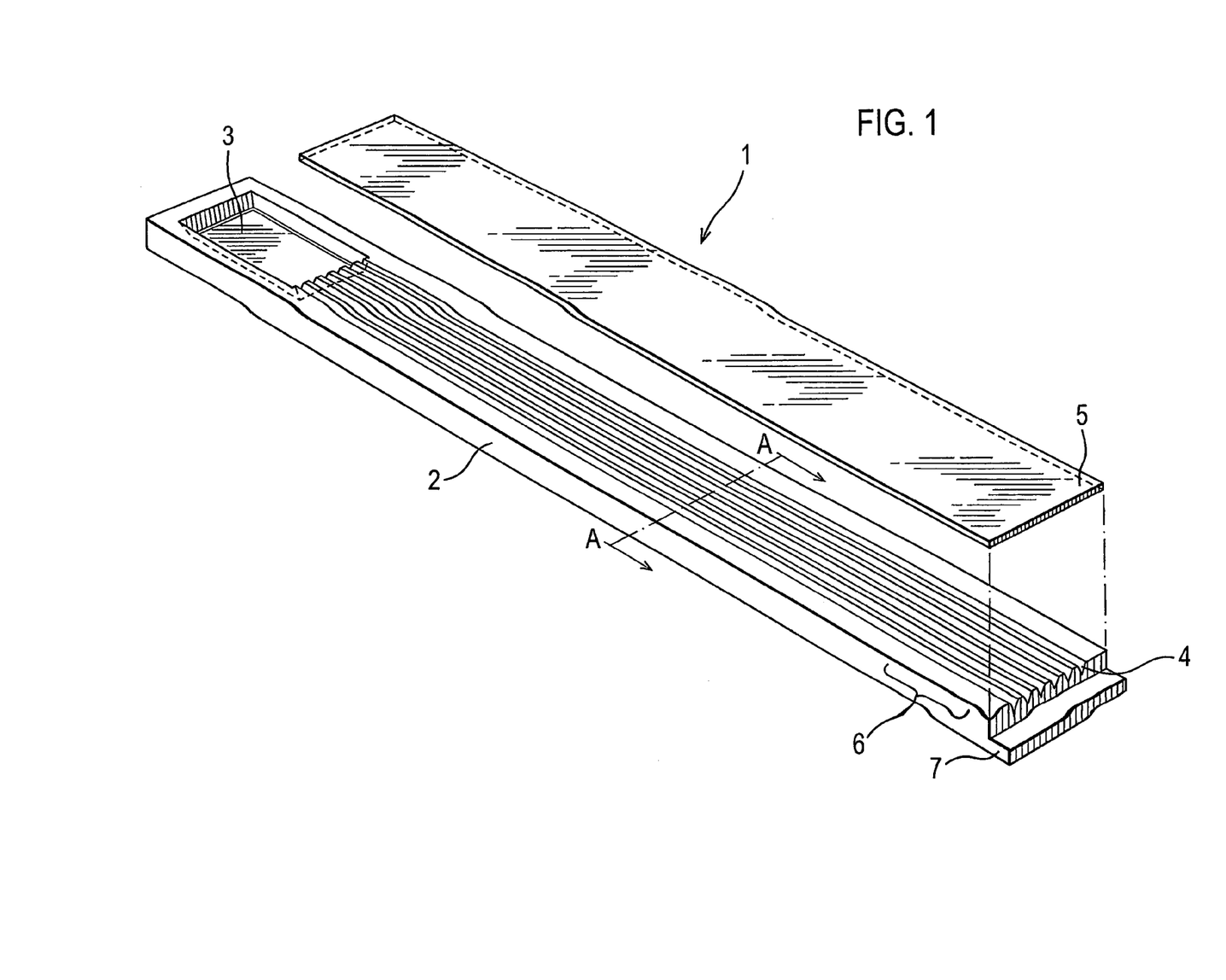
Figure 2:
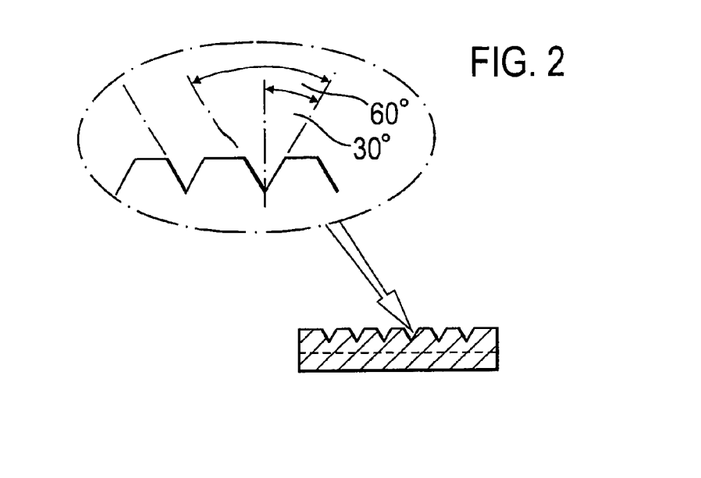
FIG. 2 is a sectional view along the line A-A of FIG. 1.

The test device 1 illustrated in FIG. 1 comprises a moulded, light transparent (clear) body 2 having upper and lower major surfaces. The upper surface is moulded towards one end thereof with a sample well 3 from which extend in parallel a plurality of V-shaped pathways 4 also moulded in the upper surface. As shown in FIG. 2, each such pathways 4 has an apical angle of 60° with each side (as viewed in section) being of equal length, preferably in the range of 0.1-1.3 mm. The pathways 4 are intended to provide two sides of a triangular capillary pathway that is completed by a cover sheet 5 which is adhesively bonded to the body 2. This cover sheet may, for example, be a polyester membrane and is bonded to the body 2 by means of an adhesive of the type described more fully above. With the cover sheet in position, blood introduced into the sample well 3 is able to flow (by capillary action) towards the downstream ends of the capillary pathways.

Body 2 may be of a hydrophobic plastics material and prior to construction of the device may be treated with a hydrophilic reagent, e.g. a 0.1-10% solution of Tween 20. Appropriate agglutination reagent systems (preferably monoclonal antibodies) are laid in the capillary pathways upstream of the individual channels 4 for arresting blood flow having a particular blood group characteristic (as described more fully above).

The capillary pathways each have a downstream detection region over the length represented by reference numeral 6 shown in the drawings somewhat downstream of the aforementioned reagent system.

The downstream end of body 2 has a step formation 7 for mounting in the reader.

Five capillary channels are formed and may be designated as follows:

| Capillary Pathway No | Reagent Arrests Blood with Characteristic | Reagent System |
| --- | --- | --- |
| No 1 | Group A | Anti-A |
| No 2 | Group B | Anti-B |
| No 3 | Group 0 | None |
| No 4 | Rhesus + ve | Anti-D |
| No 5 | Control | None (optional) |

As explained more fully above, blood will reach the detection region of the Control Pathway No 5 (provided the device is functioning properly) and also the detection regions of some but not all of the other tracks in a pattern that is dependent on the blood characteristic of the blood under test.

Figure 3:
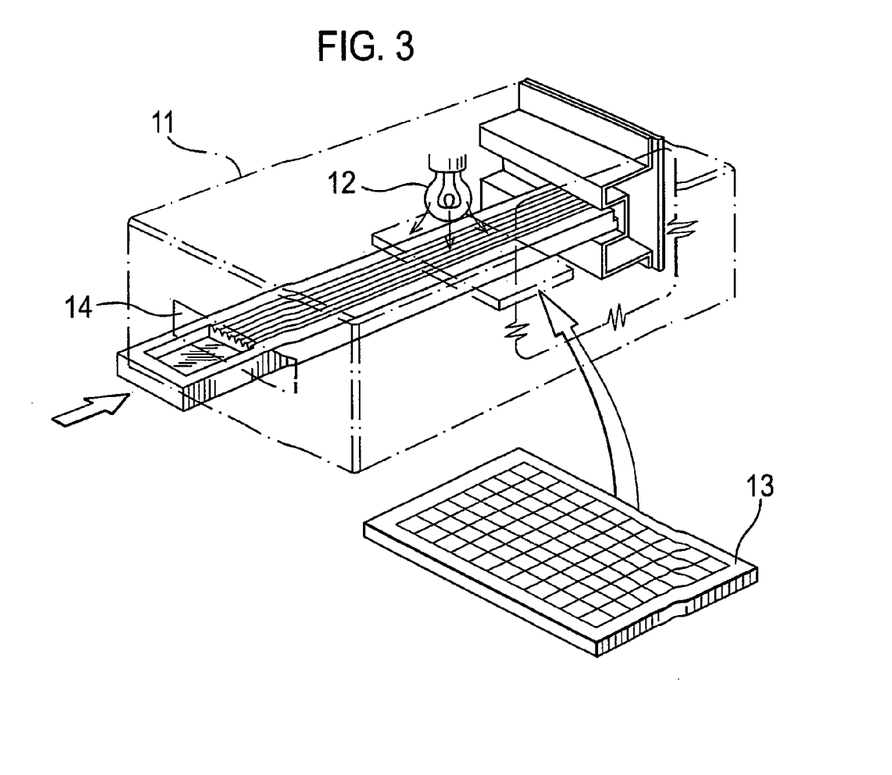
FIG. 3 schematically illustrates, to a much reduced scale, detection of a test result in accordance with the invention.
Figure 4:
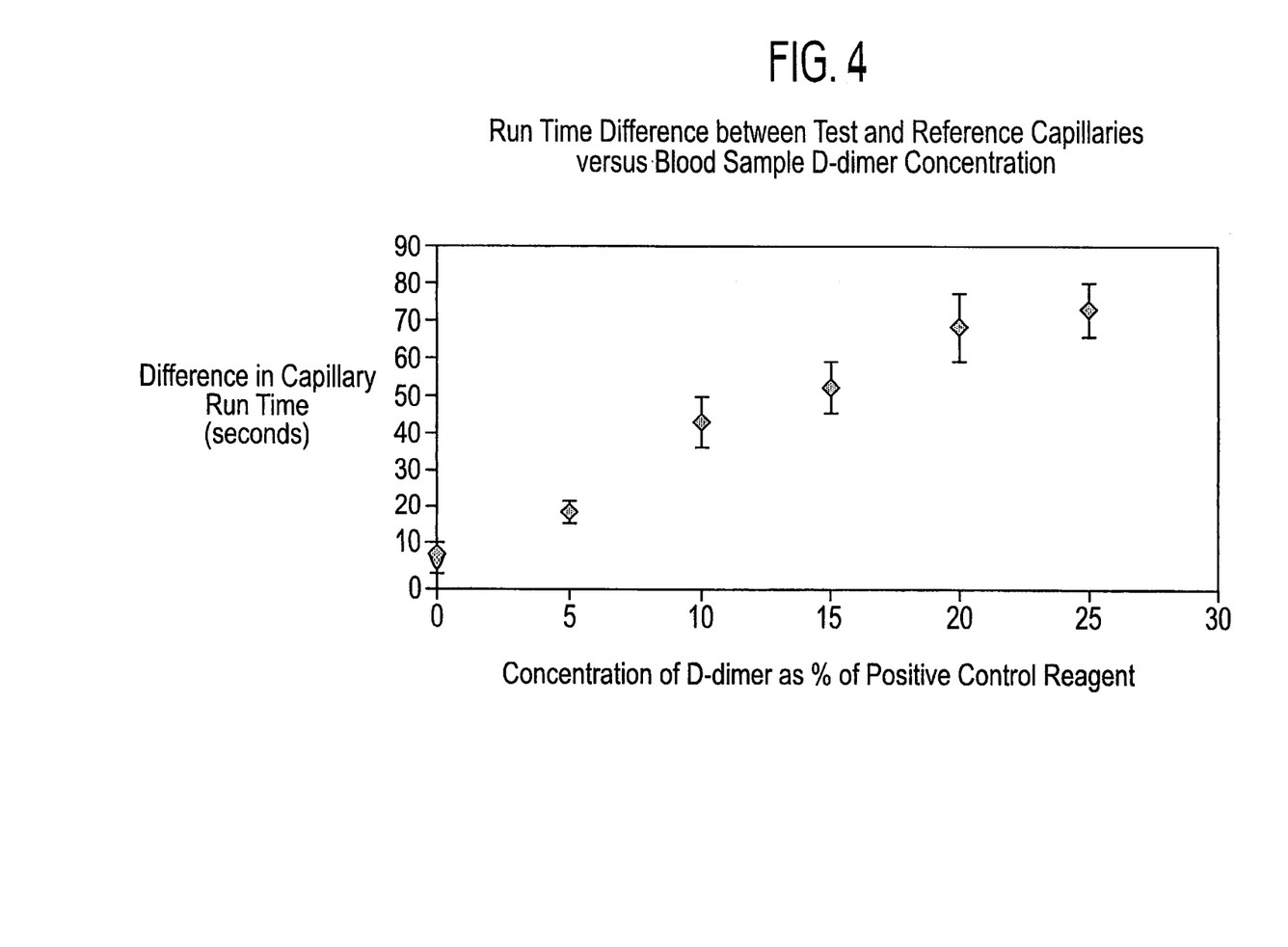
FIG. 4 is a graph showing the results of an assay according to the invention.

FIG. 3 illustrates a reader for determining the result of the test. This arrangement comprises a casing 11 having an internal upper illumination source 12 (e.g. a LED) and a lower detector array 13 of light sensitive elements. The casing further has a slot 14 into which the test device 1 may be inserted until it locates (by means of the step formation 7) into a corresponding internal recess at the rear of the casing 11 to ensure correct location of the unit 1 for the detection operation. More particularly, this involves positioning of the detection region 6 of the unit 1 beneath the illumination source 12 and above the detector array 13.

The purposes of the detection operation, source 12 is illuminated and the pattern of light transmitted through the unit 1 to the array 13 is detected, this pattern identifying the blood group characteristic of the sample under test, as described more fully above.

Detector array 13 is thus capable of providing an electronic signal that identifies the blood group characteristic. This signal may then be employed in a patient management system, as described more fully above.

A capillary agglutination test was developed using commercially available haemagglutination kit reagents (AGEN SimpliRED™ D-dimer test).

Preparation of Test Devices:

Capillary test beds were prepared for deposition of reagents by washing with 50% ethanol, followed by 0.25% Tween 20. Haemagglutination reagent (AGEN SimpliRED™ D-dimer 'test reagent') (5 µl) was pipetted into the capillary 'test' track approximately half-way along its length. The capillary 'reference' track was left empty. Following deposition of reagent, test beds were desiccated and sealed, using adhesive tape, prior to performing the test procedure.

Sample Preparation:

Samples for use in the D-dimer test were prepared as follows:

Whole human donor blood was separated into cells/plasma fractions and 25% of the total volume (plasma fraction) was replaced with D-dimer analyte (AGEN SimpliRED™ D-dimer 'positive control') and/or 10 mM phosphate buffered saline pH 7.4, 0.5% bovine serum albumin, such that a series of 'simulated' D-dimer positive blood samples, containing D-dimer concentrations between 0% and 25% (of the positive control reagent concentration) were generated.

Test Procedure:

The capillary agglutination test procedure was carried-out in the following way:

(i) 20 µl of sample blood was introduced to the start area of the prepared test device. (The fluid was drawn into the first 10 cm of the tracks by capillary action—approximately 10 µl into each track).

(ii) After 2 minutes, 180 µl of 10 mM phosphate buffered saline pH 7.4 was introduced to the fluid reservoir of the device. (This caused the capillary flow to resume).

(iii) Time taken for the fluids to reach the end of the test and reference capillary tracks were recorded.

D-Dimer Dose-Response Experiment:

Test devices were prepared according to example 1, using AGEN SimpliRED™ D-dimer test haemagglutination reagent. Human whole blood samples, containing a range of D-dimer concentrations between 0% and 25% (with respect to the AGEN SimpliRED™ D-dimer test positive control) were prepared according to example 2. The test procedure was carried out according to example 3 and test and reference lane run times were recorded (n=10). The difference between test and reference capillary run times was plotted against 'simulated' sample D-dimer concentration (FIG. 1).

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

The invention claimed is:

1. A test device for use in an agglutination based assay for determining the presence and/or amount of analyte in a sample, comprising one or more capillary pathways which receive the sample and/or reagent and which extend from an upstream end toward a downstream end and which comprise one or more detection regions, wherein the test device is releasably mountable in a reader which comprises detection means for non-visual detection of liquid at one or more of the detection regions in each of said capillary pathways to provide a measurement of time and/or rate of liquid flow to the detection regions, and electronic means for indicating the presence and/or amount of analyte based upon the pattern.

2. An agglutination based assay system for determining the presence and/or amount of analyte in a sample comprising:
   (a) a test device comprising at least two capillary pathways, at least one being an assay pathway and one being a control pathway for comparison with the assay pathway, wherein the pathways each extend from an upstream end where the sample is received toward a downstream end and wherein each of the pathways comprise more than one detection region at predetermined positions at which the presence or absence of liquid is determined whereby a pattern of liquid flow to the detection regions is obtained that indicates the rate of flow along the pathways; and
   (b) a reader comprising detection means for non-visual detection of liquid at the detection regions in each capillary pathway as a yes/no indication, and electronic means for indicating the amount of analyte based upon a comparison of the measurement of time and/or rate of liquid flow in the control pathway and the measurement of time and/or rate of liquid flow in the assay pathway.

3. An agglutination based assay system according to claim 2 comprising a zone at the upstream end for receiving the sample and/or reagents.

4. An agglutination based assay system according to claim 3 comprising a one-way valve at the entrance to the capillary pathways, so that the sample/reagents applied to the zone can enter, but not exit, the pathways upon opening of the valve.

5. An agglutination based assay system according to claim 2 comprising means for releasably mounting the reader.

6. An agglutination based assay system according to claim 2 comprising at least one agglutination reagent pre-applied to the assay pathway.

7. An agglutination based assay system according to claim 2, wherein the detection regions are positioned downstream of any pre-applied agglutination reagent.

8. An agglutination based assay system according to claim 2 wherein the detection means is selected from the group consisting of: optical means; reflectometers; measurement of light scattering; fluid detection; turbidometry; electrical means and nephelometry.

9. An agglutination based assay system according to claim 8 wherein the detection means is an electronic optical detection means and comprises an array of Light Dependent Diodes (LDDs) or Light Sensitive Resistors.

10. An agglutination based assay system according to claim 9 wherein the electronic optical detector is of the type used for reading barcodes by light transmission.

11. An agglutination based assay system according to claim 2 wherein the detection means is programmed to detect the presence of sample reaching a detection region by way of confirmation that the device is functioning properly.

12. An agglutination based assay system according to claim 2 wherein the detection means is programmed to detect the presence of sample at an upstream region of the control capillary pathway by way of a confirmation that the unit is functioning properly.

13. An agglutination based assay system according to claim 2 wherein the electronic means comprises signal processing means and display means.

14. An agglutination based assay system according to claim 13 wherein the signal processing means comprises a timer which is activated at an appropriate point in the assay.

15. An agglutination based assay system according to claim 2, further comprising an agglutination reagent that comprises a binding partner having a preferential affinity for the analyte to be detected, bound to an agglutination particle.

16. An agglutination based assay system according to claim 15, wherein the binding partner is selected from the group consisting of: a monoclonal or polyclonal antibody, antigen, protein, enzymes, binding proteins, aptamers, oligonucleotides, sugars, and fragments thereof.

17. An agglutination based assay system according to claim 15 wherein the particle bound to the binding partner is selected from the group consisting of: microorganisms, cells, macromolecules, gold particles, beads, charcoal, kaolinite, and bentonite.

18. An agglutination based assay system according to claim 17, wherein the agglutination particle is a red blood cell.

19. An agglutination based assay system according to claim 18 wherein the agglutination reagent system is a heme based system.

20. An agglutination based assay system according to claim 2, wherein the sample is selected from the group consisting of: urine, whole blood, a blood fraction, plasma, semen, sweat, saliva, amniotic fluid, cerebrospinal fluid, pleural fluid, gingival fluid, cyst extract and tissue extracts.

21. An agglutination based assay system according to claim 2, wherein the analyte is selected from the group consisting of: antigen, antibody, oligonucleotide, hormone, aptamer, sugar, or combinations and fragments thereof, organisms, fungus, bacteria, viruses, protozoa, multicellular parasites, or fragments thereof, and therapeutic and non-therapeutic drugs.

22. A kit comprising one or more test device according to claim 1 and sufficient reagent to conduct the same number of assays.

23. A kit according to claim 22 additionally comprising at least one element selected from the group consisting of: a reader, buffer, reagent, application means, instructions, charts, desiccants, control samples, dyes, batteries, and signal processing/display means.

24. A system for determining the blood group characteristic of a blood sample comprising:
   i) a test device having a plurality of separate test capillary pathways and a control capillary pathway along each of which blood will flow from upstream to downstream ends thereof, said test capillary pathways and said control capillary pathway each having more than one detection regions at which the presence or absence of blood is detected, and said test capillary pathways further including reagents which will cause agglutination of blood in at least one but not all, of the test capillary pathways in a combination dependent upon the blood group characteristic of the blood sample;

ii) detection means for detecting the presence or absence of blood at the detection regions in each of said test capillary pathways and said control capillary pathway as a yes/no indication so as to provide a measurement of time and/or rate of blood flow to the detection regions; and iii) electronic means for identifying the blood group characteristic from the measurement of time and/or rate of blood flow.

25. A method of determining the blood group of a blood sample, comprising the steps of:
i) providing a system according to claim 24
ii) introducing into an upstream end of each capillary pathway reagents which will cause agglutination of blood in at least one but not all of the pathways, in a combination dependent upon the blood group characteristic of the blood;
iii) introducing blood into an upstream end of the capillary pathways;
iv) detecting the presence of blood at detection regions of the capillaries so as to determine a measurement of time and/or rate of blood flow within the capillary pathways; and
v) using electronic means to identify the blood group characteristic from the measurement of time and/or rate determined in iii).

26. A method according to claim 25 wherein step iv) provides an electronic signal to a patient management system which incorporates electronic processing and storage means which:
(a) stores the recorded (previously determined) blood group characteristic of the donated blood under test;
(b) electronically receives the result of the blood group characteristic of the donated blood from the system;
(c) compares the information for (a) and (b) to confirm or otherwise that the blood to be donated is of the same blood group characteristic as previously recorded;
(d) stores information about the blood group characteristic of the patient to whom the blood is to be donated; and
(e) provides a warning output if the blood is of the wrong type for administration to the patient.

27. A system for determining the blood group characteristic of a blood sample according to claim 24, comprising at least three assay capillary pathways.

28. A system for determining the blood group characteristic of a blood sample according to claim 24, wherein the reagents are monoclonal antibodies.

* * * * *